(12) United States Patent
Stopp et al.

(10) Patent No.: US 10,918,444 B2
(45) Date of Patent: Feb. 16, 2021

(54) VIDEO BASED PATIENT REGISTRATION AND TRACKING

(71) Applicant: Brainlab AG, Munich (DE)

(72) Inventors: Sebastian Stopp, Munich (DE); Johannes Manus, Munich (DE)

(73) Assignee: BRAINLAB AG, Munich (DE)

( * ) Notice: Subject to any disclaimer, the term of this patent is extended or adjusted under 35 U.S.C. 154(b) by 0 days.

(21) Appl. No.: 16/628,848

(22) PCT Filed: Jul. 11, 2018

(86) PCT No.: PCT/EP2018/068792
§ 371 (c)(1),
(2) Date: Jan. 6, 2020

(87) PCT Pub. No.: WO2019/029934
PCT Pub. Date: Feb. 14, 2019

(65) Prior Publication Data
US 2020/0197101 A1    Jun. 25, 2020

(30) Foreign Application Priority Data

Aug. 11, 2017   (WO) ................. PCT/EP2017/070493

(51) Int. Cl.
*A61B 34/20*        (2016.01)
*H04N 5/247*        (2006.01)
(Continued)

(52) U.S. Cl.
CPC ............. *A61B 34/20* (2016.02); *A61B 46/20* (2016.02); *A61B 90/20* (2016.02); *G06T 7/0012* (2013.01);
(Continued)

(58) Field of Classification Search
None
See application file for complete search history.

(56) References Cited

U.S. PATENT DOCUMENTS

2005/0123289 A1   6/2005   Schweikard
2011/0015518 A1*  1/2011   Schmidt ................. A61B 34/10
                                                                600/424
(Continued)

FOREIGN PATENT DOCUMENTS

EP         0672389 A2    9/1995
WO     2014139022 A1    9/2014
(Continued)

OTHER PUBLICATIONS

International Search Report for corresponding international application No. PCT/EP2018/068792, dated Nov. 16, 2018. 6 Pages.

*Primary Examiner* — Christopher Braniff
(74) *Attorney, Agent, or Firm* — Tucker Ellis LLP

(57) ABSTRACT

A computer implemented method and a system for registering and tracking an anatomical structure of a patient. A method includes acquiring a first stereoscopic image dataset including video images having different viewing angles, and providing a first image content showing the anatomical structure; registering the first image dataset to a 3D image dataset showing the anatomical structure; acquiring a second stereoscopic image dataset comprising video images having different viewing angles and providing a second image content showing the anatomical structure, which differs from the first image content; and tracking the anatomical structure based on the second image dataset.

19 Claims, 3 Drawing Sheets

(51) Int. Cl.
    *H04N 13/204*    (2018.01)
    *A61B 46/20*     (2016.01)
    *A61B 90/20*     (2016.01)
    *G06T 7/292*     (2017.01)
    *G06T 7/246*     (2017.01)
    *G06T 7/00*      (2017.01)
    *A61B 90/00*     (2016.01)

(52) U.S. Cl.
    CPC .............. *G06T 7/246* (2017.01); *G06T 7/292* (2017.01); *H04N 5/247* (2013.01); *H04N 13/204* (2018.05); *A61B 2034/2057* (2016.02); *A61B 2034/2065* (2016.02); *A61B 2090/364* (2016.02); *A61B 2090/371* (2016.02); *A61B 2090/3937* (2016.02); *G06T 2207/10012* (2013.01); *G06T 2207/10056* (2013.01); *G06T 2207/30204* (2013.01)

(56) References Cited

U.S. PATENT DOCUMENTS

2017/0143430 A1    5/2017  Miga
2017/0171456 A1*   6/2017  Wei ...................... H04N 13/239

FOREIGN PATENT DOCUMENTS

WO    2016041051 A1    3/2016
WO    2016058088 A1    4/2016

* cited by examiner

VIDEO BASED PATIENT REGISTRATION AND TRACKING

RELATED APPLICATION DATA

This application is a national phase application of International Application No. PCT/EP2018/068792 filed Jul. 11, 2018, which claims priority to International Application No. PCT/EP2017/070493 filed on Aug. 11, 2017, the contents of both of which are incorporated herein by reference.

TECHNICAL FIELD

The present invention relates to a computer implemented method for registering and tracking an anatomical structure of a patient based on video images. The present invention further relates to a corresponding computer program and a corresponding system for registering and tracking an anatomical structure of a patient based on video images.

BACKGROUND

In the context of image guided surgery (IGS), it is necessary for an assisting navigation system to know at the spatial position of anatomical structures in real space, which correspond to structures shown in an image data set such as a MRI-data set or a CT-data set acquired. For this purpose, a so-called patient registration procedure is initially performed. Known approaches for patient registration, particularly for navigated cranial surgeries may for example involve landmark registration methods in which easily identifiable anatomical landmarks of the patient are palpated with a tracked pointer instrument prior to the medical treatment. Since the spatial position of the tip of such instrument is known to a medical tracking system associated with a medical navigation system, and since the position of the corresponding image of the palpated landmarks within virtual image space is known to the medical navigation system, as well, a complete registration of a rigid anatomical structure may be obtained by palpating and storing the spatial position of at least three different anatomical landmarks. In case the anatomical structure in questions maintains its spatial position, such registration would be sufficient to perform image guided surgery on that structure. However, anatomical structures may change their spatial position over time, either accidentally or intentionally. It is therefore further necessary to perform a so-called tracking procedure in order to determine the current spatial position at every point in time, which may have changed or deviated from an initially determined spatial position. Known tracking solutions involve the use of tracking markers which are rigidly attached to each object of interest that may change its position over time, including anatomical structures, medical devices, medical instruments and the like. For optical tracking solutions, i.e. tracking systems that utilize optically recognizable tracking markers it has to be ensured that the line of sight between those tracking markers and the at least one optical camera of the tracking systems remains uninterrupted during the entire medical procedure. This requirement is often inconvenient for medical personnel who already have to accomplish their medical tasks.

SUMMARY

The present invention provides a computer implemented method and a corresponding system which has been improved at least in regards to the line of sight issues optical tracking systems are generally subjected to. Specifically, the present invention takes advantage of the uninterrupted line of sight provided for a surgical microscope in order to observe anatomical structures of interest.

The inventive computer implemented registering and tracking method comprises the steps of
- acquiring a first stereoscopic image dataset comprising video images having different viewing angles and providing a first image content showing the anatomical structure;
- registering said first image dataset to a 3D image dataset showing the anatomical structure;
- acquiring a second stereoscopic image dataset comprising video images having different viewing angles and providing a second image content showing the anatomical structure, which differs from the first image content;
- track the anatomical structure based on the second image dataset.

In other words, a first of set of stereoscopic video images is acquired from the patient's body part of interest in an initial method step. This first image data set has an image content showing the anatomical structure, which is then used to register the first image data set to a for example previously acquired three-dimensional image data set. This can be done by calculating the three-dimensional position of at least three optically detectable features on the surface of the anatomical structure from the position of these features in each of the two stereoscopic images. As soon as the spatial position of the at least three features in real space has been calculated, a three-dimensional image data set can be searched for the corresponding images of these three features, whereupon the "real" anatomical structure can be matched to its virtual, previously acquired three-dimensional image, thereby completing the initial registration procedure.

After the anatomical structure has been registered to a virtual image data set image guided surgery can be performed while at the same time the anatomical structure is tracked on the basis of stereoscopic video images, as well. As already set out above, the three-dimensional position of optically recognizable features can be calculated from the stereoscopic images such that the spatial position of each feature can be tracked over time.

Summarizing the above, it can be said that both, the registration of the anatomical structure with a previously acquired three-dimensional data set as well as tracking the anatomical structure in real space is based on stereoscopic video images obtained from a stereoscopic camera array, which may even be same stereoscopic camera array.

However, the image content of the stereoscopic image data set, i.e. the sum of the features of the anatomical structure which are visible to the camera array often changes over time in the progression of the medical workflow. Thus, image content which is available during a registration procedure may sometimes not be available anymore for the tracking procedure that follows. For example, covering the anatomical structure with a surgical drape significantly reduces the amount of image data that can be used for calculating the three-dimensional position of features shown in the video images. In fact, current surgical procedures usually require that the patient is draped after having been registered.

The available image content is also reduced by surgery itself. For example, any resection that alters the optical appearance of the anatomical structure and even blood or other body fluids covering the anatomical structure lead to a change or even reduction of available image data.

Consequently, the inventive registration and tracking method has to rely on optically detectable features that can be recognized during the registration procedure as well as during the tracking procedure.

For this purpose, specific reference structures are defined which generally may be either natural, i.e. belonging to the anatomical structure itself, or artificial, i.e. being specifically provided and attached to the anatomical structure for registration and tracking purposes. Basically, any optically recognizable feature may serve as a reference structure as long as it maintains its spatial position with respect to the anatomical structure and can be recognized by the video cameras during registration and tracking.

Thus, the inventive method may involve registering the anatomical structure shown in the second image data set to at least one designated reference structure that is trackable, rigidly coupled to the anatomical structure and shown in the second image data set, and which is particular specifically adapted to be tracked via video tracking.

Further, the at least one reference structure, which may be the same reference structure as seen in the second image data set, is shown in the first image data set and is utilized to register the anatomical structure shown in the first image data set to the three-dimensional image data set.

In a specific embodiment of the present invention the at least one reference structure may comprise optical, particularly retro reflective tracking markers.

According to a further embodiment of the present invention the stereoscopic camera array is rigidly coupled to a surgical microscope such that it can take advantage of the uninterrupted line of sight that is provided for observation purposes between the surgical microscope and the anatomical structure anyway. In the alternative, the stereoscopic camera array may however also be provided separately to the surgical microscope and may for example be supported by an articulated support arm next to the operation site.

Further, the camera array may comprise at least one camera that is already incorporated into the optical path of the surgical microscope, i.e. an internal camera of a surgical microscope as it is already known from prior art surgical microscopes. Additionally or alternatively, the camera array may also comprise at least one camera that is rigidly attached to the surgical microscope, for example the housing of the surgical microscope. In order to ease the registration and/or tracking procedures, the computational burden may be reduced by utilizing cameras that have a fixed zoom and/or a fixed focus.

In a specific embodiment of the present invention, the anatomical structure may comprise two different visible surfaces that lie above each other, wherein the first surface is exclusively shown in the first image data set and the second surface is exclusively shown in the second image data set. This is for example the case for craniotomy, which involves removing a bone flap from the skull to access the brain. Thus, the first surface may be the skin on the skull of a patient, whereas the second surface may be the brain surface as seen through the opening in the skull.

In this respect, a positional change between a first part and a second part of the anatomical structure (for example the positional change between the brain and the skull) can be determined as compared to the initial spatial position which is shown in the three-dimensional image data set prior to surgery. The so-called "brain shift" may involve any positional change of the brain with respect to the skull, including a motion of the brain within the skull as well as a "swelling" of the brain out of the opening in the skull.

A further aspect of the present invention relates to a computer program which, when running on a computer, causes the computer to perform the method steps referred in any one of the embodiments described above. A further aspect relates to a corresponding program storage medium on which such program is stored, in particular in a non-transitory form, wherein the invention may further relate to a signal wave carrying information which represents this program.

An even further aspect of the present invention relates to a registering and tracking system comprising a camera array and a computer as described in several embodiments above.

The method, the program and the system are defined by the appended independent claims. Advantages, advantageous features, advantageous embodiments and advantageous aspects of the present invention are disclosed in the following and contained in the subject-matter of the dependent claims. Different advantageous features can be combined in accordance with the invention wherever technically expedient and feasible. Specifically, a feature of one embodiment which has the same or a similar function to another feature of another embodiment can be exchanged with said other feature, and a feature of one embodiment which adds an additional function to another embodiment can in particular be added to said other embodiment.

Definitions

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing (medical) imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is an augmented reality device (also referred to as augmented reality glasses) which can be used as "goggles" for navigating. A specific example of such augmented reality glasses is Google Glass (a trademark of Google, Inc.). An augmented reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. The monitor may also be the monitor of a portable, for example handheld, device such as a smart phone or personal digital assistant or digital media player.

The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing (and e.g. outputting) the data by means of a computer and for example within the framework of the method in accordance with the invention. The meaning of "acquiring data" also for example encompasses the scenario in which the data are received or retrieved by (e.g. input to) the computer implemented method or program, for example from another program, a previous method step or a data storage medium, for example for further processing by the computer implemented method or program. Generation of the data to be acquired may but need not be part of the method in accordance with the invention. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

The n-dimensional image of a body is registered when the spatial location of each point of an actual object within a space, for example a body part in an operating theatre, is assigned an image data point of an image (CT, MR, etc.) stored in a navigation system.

Image registration is the process of transforming different sets of data into one co-ordinate system. The data can be multiple photographs and/or data from different sensors, different times or different viewpoints. It is used in computer vision, medical imaging and in compiling and analyzing images and data from satellites. Registration is necessary in order to be able to compare or integrate the data obtained from these different measurements.

The invention also relates to a program which, when running on a computer, causes the computer to perform one or more or all of the method steps described herein and/or to a program storage medium on which the program is stored (in particular in a non-transitory form) and/or to a computer comprising said program storage medium and/or to a (physical, for example electrical, for example technically generated) signal wave, for example a digital signal wave, carrying information which represents the program, for example the aforementioned program, which for example comprises code means which are adapted to perform any or all of the method steps described herein.

The invention also relates to a navigation system for computer-assisted surgery, comprising:

the computer of the preceding claim, for processing the absolute point data and the relative point data;

a detection device for detecting the position of the main and auxiliary points in order to generate the absolute point data and to supply the absolute point data to the computer;

a data interface for receiving the relative point data and for supplying the relative point data to the computer; and a user interface for receiving data from the computer in order to provide information to the user, wherein the received data are generated by the computer on the basis of the results of the processing performed by the computer.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

It is the function of a marker to be detected by a marker detection device (for example, a camera or an ultrasound receiver or analytical devices such as CT or MRI devices) in such a way that its spatial position (i.e. its spatial location and/or alignment) can be ascertained. The detection device is for example part of a navigation system. The markers can be active markers. An active marker can for example emit electromagnetic radiation and/or waves which can be in the infrared, visible and/or ultraviolet spectral range. A marker can also however be passive, i.e. can for example reflect electromagnetic radiation in the infrared, visible and/or ultraviolet spectral range or can block x-ray radiation. To this end, the marker can be provided with a surface which has corresponding reflective properties or can be made of metal in order to block the x-ray radiation. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can however also exhibit a cornered, for example cubic, shape.

A marker device can for example be a reference star or a pointer or a single marker or a plurality of (individual) markers which are then preferably in a predetermined spatial relationship. A marker device comprises one, two, three or more markers, wherein two or more such markers are in a predetermined spatial relationship. This predetermined spatial relationship is for example known to a navigation system and is for example stored in a computer of the navigation system.

In another embodiment, a marker device comprises an optical pattern, for example on a two-dimensional surface. The optical pattern might comprise a plurality of geometric shapes like circles, rectangles and/or triangles. The optical pattern can be identified in an image captured by a camera, and the position of the marker device relative to the camera can be determined from the size of the pattern in the image, the orientation of the pattern in the image and the distortion of the pattern in the image. This allows determining the relative position in up to three rotational dimensions and up to three translational dimensions from a single two-dimensional image.

The position of a marker device can be ascertained, for example by a medical navigation system. If the marker device is attached to an object, such as a bone or a medical instrument, the position of the object can be determined from the position of the marker device and the relative position between the marker device and the object. Determining this relative position is also referred to as registering the marker device and the object. The marker device or the object can be tracked, which means that the position of the marker device or the object is ascertained twice or more over time.

The present invention is also directed to a navigation system for computer-assisted surgery. This navigation system preferably comprises the aforementioned computer for processing the data provided in accordance with the computer implemented method as described in any one of the embodiments described herein. The navigation system preferably comprises a detection device for detecting the position of detection points which represent the main points and auxiliary points, in order to generate detection signals and to supply the generated detection signals to the computer, such that the computer can determine the absolute main point data and absolute auxiliary point data on the basis of the detection signals received. A detection point is for example a point on the surface of the anatomical structure which is detected, for example by a pointer. In this way, the absolute point data can be provided to the computer. The navigation system also preferably comprises a user interface for receiving the calculation results from the computer (for example, the position of the main plane, the position of the auxiliary plane and/or the position of the standard plane). The user interface provides the received data to the user as information. Examples of a user interface include a display device such as a monitor, or a loudspeaker. The user interface can use any kind of indication signal (for example a visual signal, an audio signal and/or a vibration signal). One example of a display device is an augmented reality device (also referred to as augmented reality glasses) which can be used as so-called "goggles" for navigating. A specific example of such augmented reality glasses is Google Glass (a trademark of Google, Inc.). An augmented reality device can be used both to input information into the computer of the navigation system by user interaction and to display information outputted by the computer.

A navigation system, such as a surgical navigation system, is understood to mean a system which can comprise: at least one marker device; a transmitter which emits electromagnetic waves and/or radiation and/or ultrasound waves; a receiver which receives electromagnetic waves and/or radiation and/or ultrasound waves; and an electronic data processing device which is connected to the receiver and/or the transmitter, wherein the data processing device (for example, a computer) for example comprises a processor (CPU) and a working memory and advantageously an indicating device for issuing an indication signal (for example, a visual indicating device such as a monitor and/or an audio indicating device such as a loudspeaker and/or a tactile indicating device such as a vibrator) and a permanent data memory, wherein the data processing device processes navigation data forwarded to it by the receiver and can advantageously output guidance information to a user via the indicating device. The navigation data can be stored in the permanent data memory and for example compared with data stored in said memory beforehand.

A medical workflow comprises a plurality of workflow steps performed during a medical treatment and/or a medical diagnosis. The workflow steps are typically, but not necessarily performed in a predetermined order. Each workflow step for example means a particular task, which might be a single action or a set of actions. Examples of workflow steps are capturing a medical image, positioning a patient, attaching a marker, performing a resection, moving a joint, placing an implant and the like.

BRIEF DESCRIPTION OF THE DRAWINGS

In the following, the invention is described with reference to the enclosed figures which represent preferred embodiments of the invention. The scope of the invention is however not limited to the specific features disclosed in the figures, which show.

DETAILED DESCRIPTION

Figure 1:
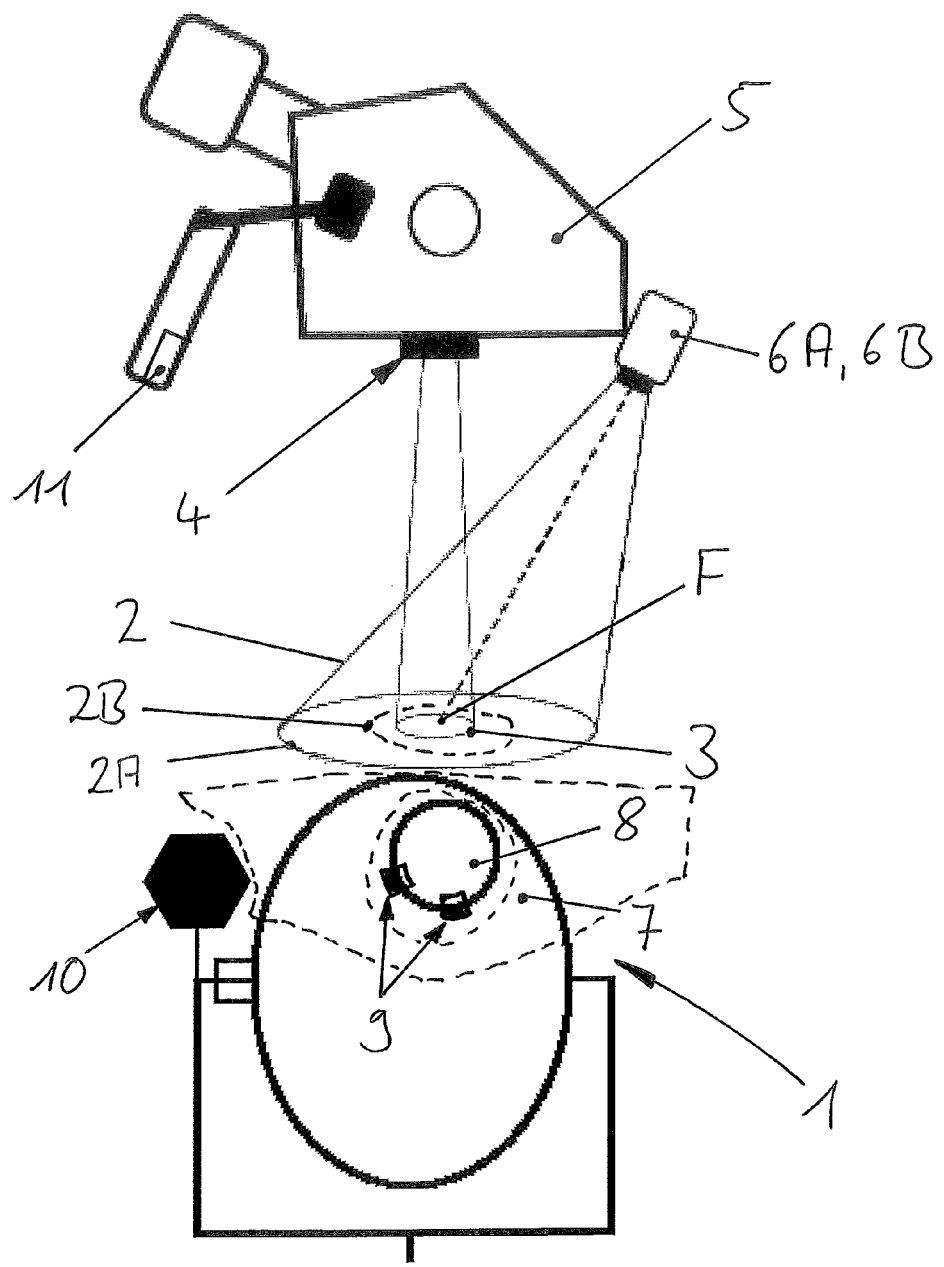
FIG. 1 a first embodiment of a registering and tracking system according to the present invention.

FIG. 1 shows a first embodiment of the inventive registering and tracking system used during craniotomy. The patient's head 1 is immobilized with the help of a Mayfield-adapter to which a reference structure 10 is rigidly coupled.

In order to obtain a detailed view on the patient's head 1, particularly on the brain 8 underneath the skull surface 7, a surgical microscope 5 is provided. This microscope 5 is equipped with a camera 4 having a field of view 3. Further, a stereoscopic camera array which comprises camera 6A and 6B with a fixed focus F and a fixed zoom is attached to the housing of the microscope. The camera array has a field of view 2 which is larger than the field of view 3 of the microscope's camera 4.

For registering the patient's head 1 with a previously acquired MRI- or CT-data set, the spatial position of visible features on the patient's head 1 is determined and registered with respect to the reference structure 10. Thus, these features and the reference structure 10 have to be situated within the image content available to the camera array. Since the head 1 of the patient is, at the time of the registration procedure, not covered by a sterile drape, the available image content 2A includes the whole two-dimensional projection of the patient's head within the image plane as well as the two-dimensional projection of the reference structure 10 within the image plane of the camera images.

After the registration procedure the patient's head 1 is covered by a sterile drape (shown in broken lines) which significantly reduces the image content 2B available to the cameras 4, 6A and 6B. Since only a small amount of the patient's head 1 can be seen through an opening in the surgical drape, the available image content 2B merely includes the reference structure 10 and the patient's head 1 as seen through the opening of the surgical drape. Thus, the tracking procedure performed during surgery with the patient's head 1 being covered has to be based on the second image content 2B which is significantly reduced with regard to the first image content 2A that had been available during the registration procedure. For tracking the patient's head 1 or even the brain surface 8, features thereof which are visible to the cameras and therefore contained in the second image content 2B are positionally determined via triangulation and the position is registered with respect to the reference structure 10. In the alternative, the position of anatomical features may be registered to any designated and optically recognizable structure such as the clamps 9 which are provided at the rim of the craniotomy.

Since the visible anatomical features are registered with respect to reference structures 9 and/or 10 the positions of which are known for both, the registration procedure and the tracking procedure, the spatial position of any optically recognizable features can be determined with respect to the three-dimensional image data set.

Figure 2:
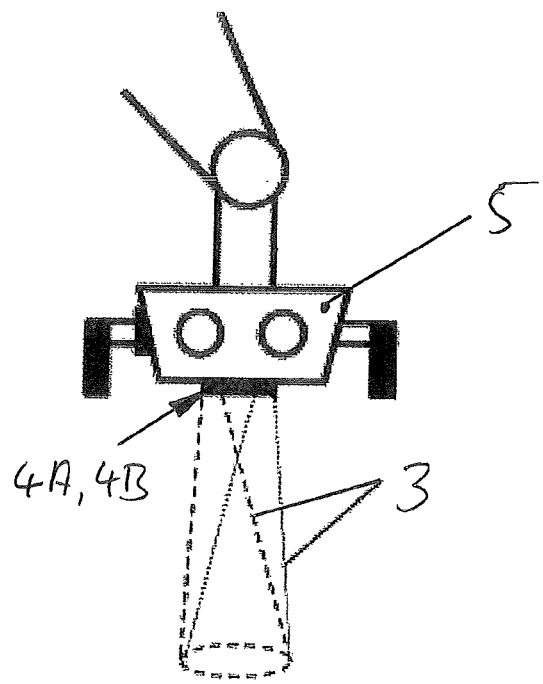
FIG. 2 a second embodiment of a registering and tracking system according to the present invention.
Figure 3:
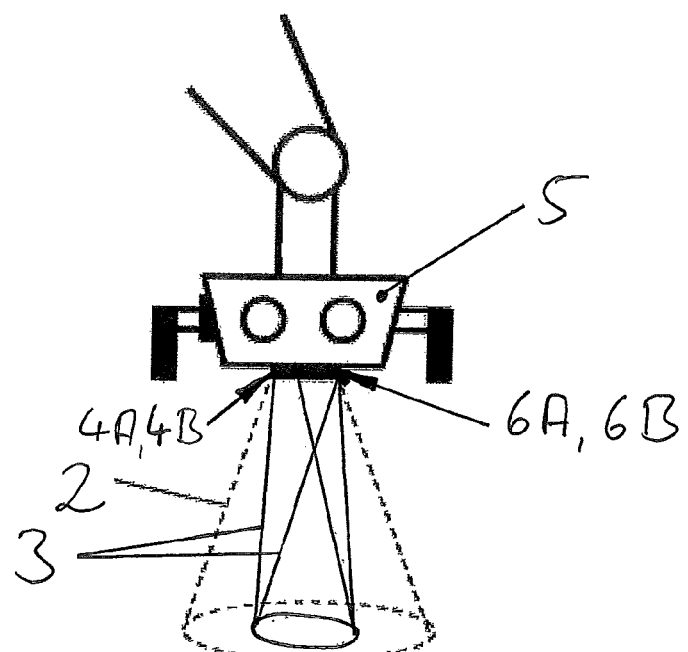
FIG. 3 a third embodiment of a registering and tracking system according to the present invention.

FIG. 2 shows an alternative embodiment which differs from the embodiment shown in FIG. 1 only in that a stereoscopic camera array assigned to the microscope 5 and comprising cameras 4A and 4B with a field of view 3 is utilized for acquired the first stereoscopic image data set and the second stereoscopic image data set. A further alternative embodiment is shown in FIG. 3, which has, in addition to the microscope's-stereoscopic camera array comprising cameras 4A and 4B, an external stereoscopic camera array with cameras 6A and 6B. Cameras 6A and 6B have a field of view 2 that is wider than the field of view 3 of the cameras 4A and 4B. Therefore, the image content available to cameras 6A and 6B covers a larger surface of the patient's anatomy.

Figure 4:
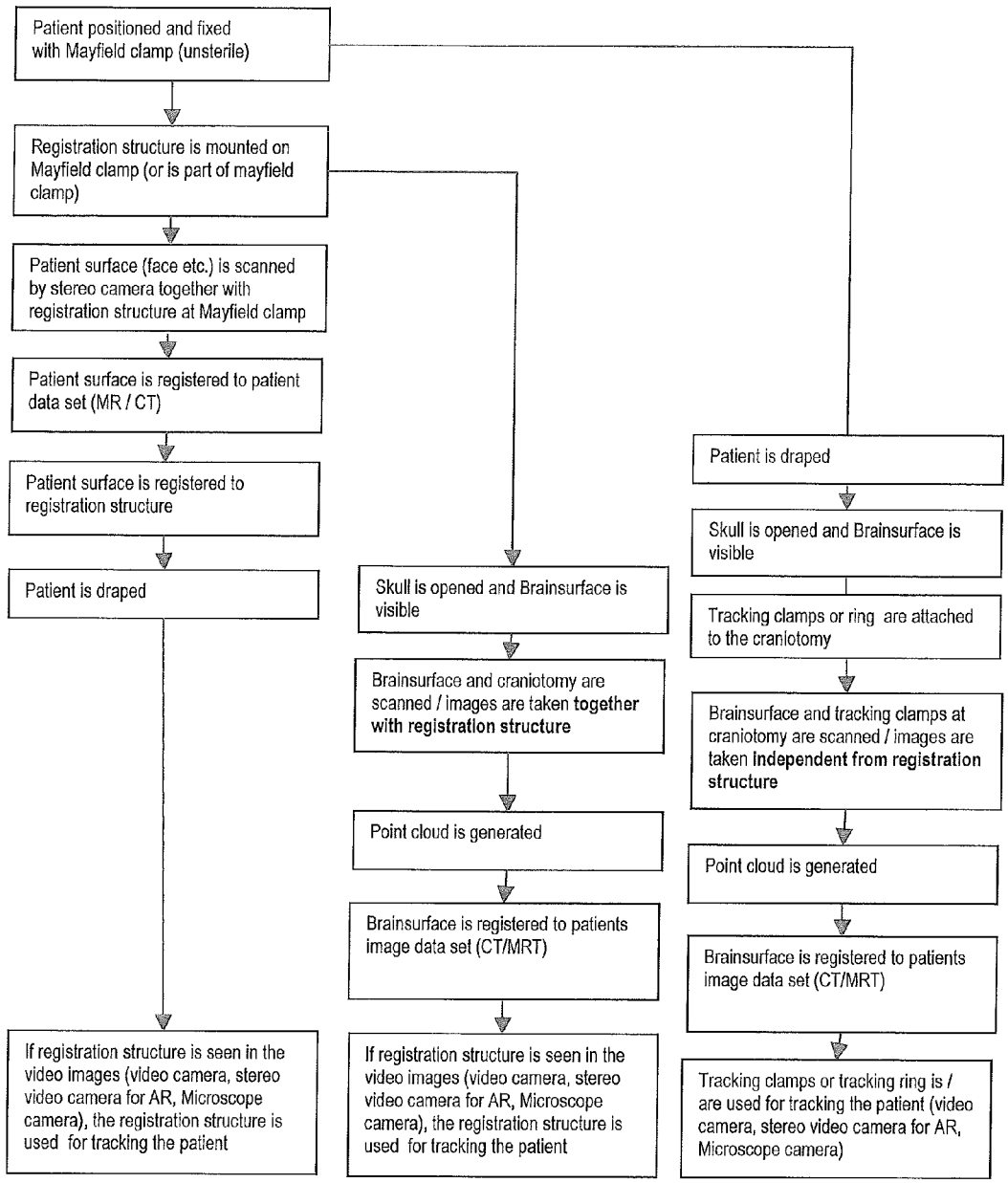
FIG. 4 a flow diagram describing three preferred methods for registering and tracking an anatomical structure of a patient in accordance with the present invention.

FIG. 4 shows three different preferred methods performed in accordance with the present invention.

The invention claimed is:

1. A computer implemented method for registering and tracking an anatomical structure of a patient, comprising:
  acquiring, via an associated camera array comprising at least two cameras, a first stereoscopic image dataset comprising video images having different viewing angles and providing a first image content showing the anatomical structure, at least one camera of the associated camera array having a fixed zoom;
  registering the first image dataset to a three-dimensional (3D) image dataset showing the anatomical structure;
  acquiring, via the associated camera array, a second stereoscopic image dataset comprising video images having different viewing angles and providing a second image content showing the anatomical structure, which differs from the first image content in that the second image content covers a smaller area of the anatomical structure than the first image content; and
  tracking the anatomical structure based on the second image dataset.

2. The method according to claim 1, wherein the associated camera array is rigidly coupled to a surgical microscope or provided separately to a surgical microscope.

3. The method according to claim 2, wherein the associated camera array comprises at least one camera incorporated into an optical path of the surgical microscope and/or at least one camera separated from the optical path of the surgical microscope and rigidly attached to the surgical microscope.

4. The method according to claim 1, wherein the first image content is changed to the second image content by draping the anatomical structure and/or by a change in the optical appearance of the anatomical structure caused by surgery.

5. The method according to claim 1, wherein the first image content differs from the second image content in that the first image content shows a different part of the anatomical structure than the second image content.

6. The method according to claim 5, wherein the first image content shows a first surface of the anatomical structure that lies above a second surface of the anatomical structure that is shown by the second image content.

7. The method according to claim 1, wherein tracking of the anatomical structure involves registering the anatomical structure shown in the second stereoscopic image dataset to at least one designated reference structure that is trackable, rigidly coupled to the anatomical structure and shown in the second stereoscopic image dataset, and which is specifically adapted to be tracked via video tracking.

8. The method according to claim 7, wherein the at least one designated reference structure is also shown in the first image dataset and is utilized to register the anatomical structure shown in the first image dataset.

9. The method according to claim 7, wherein the at least one designated reference structure comprises retro-reflective tracking-markers.

10. The method according to claim 8, wherein a relative position of a first part of the anatomical structure shown in the first image dataset to a second part of the anatomical structure shown in the second stereoscopic image dataset is detected and a change to a relative position as shown in the 3D image dataset is indicated.

11. The method according to claim 1, wherein the anatomical structure is the head of an associated patient, having different parts, which may alter their appearance and/or relative position.

12. The method according to claim 11, wherein the different parts comprise a surface of the cranium of the associated patient and a surface of the brain of the associated patient.

13. The method according to claim 1, wherein the 3D image dataset is a pre-acquired CT-dataset or pre-acquired MRI-dataset.

14. A non-transitory computer readable storage medium storing a program, which, when running on a computer or loaded onto the computer, causes the computer to:
  acquire, via an associated camera array comprising at least two cameras, a first stereoscopic image dataset comprising video images having different viewing angles and providing a first image content showing the anatomical structure, at least one camera of the associated camera array having a fixed zoom;
  register the first image dataset to a three-dimensional (3D) image dataset showing the anatomical structure;
  acquire, via the associated camera array, a second stereoscopic image dataset comprising video images having different viewing angles and providing a second image content showing the anatomical structure, which differs from the first image content in that the second image content covers a smaller area of the anatomical structure than the first image content; and
  track the anatomical structure based on the second image dataset.

15. A system for registering and tracking an anatomical structure of an associated patient, comprising:
  a camera array adapted to acquire a first stereoscopic image dataset and a second stereoscopic image dataset comprising video images taken from different viewing angles and having a first image content showing the anatomical structure and a second image content showing the anatomical structure, respectively, the camera array comprising at least two cameras, at least one camera of the associated camera array having a fixed zoom, and the second image content differing from the first image content in that the second image content covers a smaller area of the anatomical structure than the first image content; and
  a computer configured to:
    acquire, via the associated camera array, the first stereoscopic image dataset;
    register the first image dataset to a three-dimensional (3D) image dataset showing the anatomical structure;
    acquire, via the associated camera array, the second stereoscopic image dataset; and
    track the anatomical structure based on the second image dataset.

16. The system according to claim 15, further comprising a surgical microscope, wherein the camera array is rigidly coupled to the surgical microscope or provided separately to the surgical microscope.

17. The system according to claim 16, wherein the camera array comprises at least one camera incorporated into an optical path of the surgical microscope and/or at least one camera separated from the optical path of the surgical microscope and rigidly attached to the surgical microscope.

18. The system according to claim 15, further comprising at least one designated reference structure.

19. The system according to claim 18, wherein the at least one designated reference structure comprises retro-reflective tracking-markers.

* * * * *